United States Patent
Skov et al.

(10) Patent No.: US 11,925,231 B2
(45) Date of Patent: *Mar. 12, 2024

(54) SAFETY GLASSES FOR HUMAN USER; SAFETY SYSTEM

(71) Applicant: Moldex-Metric, Inc., Culver City, CA (US)

(72) Inventors: Torben Skov, Pliezhausen (DE); Roman Skov, Pliezhausen (DE)

(73) Assignee: Moldex-Metric, Inc., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/165,073

(22) Filed: Feb. 6, 2023

(65) Prior Publication Data

US 2023/0180879 A1 Jun. 15, 2023

Related U.S. Application Data

(63) Continuation of application No. 17/662,747, filed on May 10, 2022, now Pat. No. 11,638,459, which is a continuation of application No. 16/789,129, filed on Feb. 12, 2020, now Pat. No. 11,350,688.

(30) Foreign Application Priority Data

Mar. 12, 2019 (EP) .................................. 19162395

(51) Int. Cl.
*A42B 3/18* (2006.01)
*A61F 9/02* (2006.01)

(52) U.S. Cl.
CPC ................ *A42B 3/18* (2013.01); *A61F 9/026* (2013.01)

(58) Field of Classification Search
CPC ................................ A61F 9/026; A61F 9/029
See application file for complete search history.

(56) References Cited

U.S. PATENT DOCUMENTS

| | | | |
|---|---|---|---|
| 4,867,550 A | 9/1989 | Jannard | |
| 6,129,435 A | 10/2000 | Reichow et al. | |
| 10,416,475 B2 | 9/2019 | Spratt | |
| 11,350,688 B2 * | 6/2022 | Skov | A61F 9/026 |

(Continued)

OTHER PUBLICATIONS

"U.S. Appl. No. 16/789,129, Non Final Office Action dated Sep. 13, 2021", 7 pgs.

(Continued)

*Primary Examiner* — Katherine M Moran
(74) *Attorney, Agent, or Firm* — Schwegman Lundberg & Woessner, P.A.

(57) ABSTRACT

Protective goggles for human use including a pair of protective goggles for human use with at least one lens, an upper edge that is positioned against the user's forehead and a lower edge that is positioned against the user's cheek. Each of the user's eyes are covered by a separate section of lens and each of these sections extends along at least one line of curvature. It is intended that each lens section has a first and a second line of curvature that, at least in substantial part, are positioned transversely to one another, and along which the individual sections of lens extend; furthermore, that the lines of curvature of one lens section are inclined towards the lines of curvature of the other lens section in terms of their positioning.

23 Claims, 2 Drawing Sheets

(56) References Cited

U.S. PATENT DOCUMENTS

| | | | |
|---|---|---|---|
| 11,638,459 B2* | 5/2023 | Skov | A61F 9/029 2/431 |
| 2020/0046561 A1 | 2/2020 | Basora et al. | |
| 2020/0142218 A1 | 5/2020 | Mcneal et al. | |
| 2020/0288809 A1 | 9/2020 | Skov et al. | |
| 2022/0369753 A1 | 11/2022 | Skov et al. | |

OTHER PUBLICATIONS

"U.S. Appl. No. 16/789,129, Notice of Allowance dated Apr. 25, 2022", 5 pgs.
"U.S. Appl. No. 16/789,129, Response filed Jan. 11, 2022 to Non Final Office Action dated Sep. 13, 2021", 10 pgs.
"U.S. Appl. No. 17/662,747, Non Final Office Action dated Dec. 12, 2022", 7 pgs.
"U.S. Appl. No. 17/662,747, Notice of Allowance dated Jan. 19, 2023", 5 pgs.
"U.S. Appl. No. 17/662,747, Response filed Dec. 21, 2022 to Non Final Office Action dated Dec. 12, 2022", 9 pgs.
U.S. Appl. No. 16/789,129 U.S. Pat. No. 11,350,688, filed Feb. 12, 2020, Safety Glasses for Human User; Safety System.
U.S. Appl. No. 17/662,747, filed May 10, 2022, Safety Glasses for Human User; Safety System.

* cited by examiner

SAFETY GLASSES FOR HUMAN USER; SAFETY SYSTEM

BACKGROUND OF THE INVENTION

This application is a continuation of and claims the benefit or priority to U.S. application Ser. No. 17/662,747, filed May 10, 2022, which is a continuation of and claims the benefit or priority to U.S. Pat. No. 11,350,688, filed Feb. 12, 2020 which claims priority under 35 U.S.C. § 119 to European patent application EP19162395.8, filed Mar. 12, 2019, the contents of each of which are incorporated herein by reference in their entireties.

The present invention concerns a pair of protective goggles for human use with a lens, an upper edge that is positioned against the user's forehead and a lower edge that is positioned against the user's cheek, whereby each of the user's eyes is covered by a separate section of lens and each of these sections extends along at least one line of curvature.

The invention also concerns a protection system for human users with a respiratory protection mask and protective goggles.

Protective goggles of the type described above are known from prior art. They serve to protect the user's eyes from dust, chips, liquids, heat, cold and other products or elements, in particular those that are produced during the machining of a work piece and may be projected or exert force in the direction of the user.

Normally, protective goggles have a lens made from transparent material with the refractive index of a conventional glass lens, which means that the user's ability to see is unaffected or is affected only to a minor degree. The lens is typically divided into two sections, whereby each section is assigned to one of the user's eyes; that is, each of the user's eyes is covered by its own section of the lens. These sections of lens typically extend along at least one line of curvature in order to ensure the ergonomically advantageous adaptation of the goggles to the shape of the user's face. In this context, a "line of curvature" is to be understood as a line that is curved in at least one dimension and along which the profile of the lens extends. As such, the curvature of the lens is specified by the longitudinal extension of the line of curvature.

Normally, the lens has a horizontal line of curvature that, when the glasses are worn as intended, runs (for example) from one of the user's eyes to the other in a horizontal direction. This means that the lens mimics the horizontal curve of the head between the right and left eye and thus ensures an advantageous fit for the user.

To ensure that an adequate supply of ambient air is available to the eyes, to avoid the glasses fogging up, and to provide sufficient room for the user's eyelashes, the lens is usually situated at a certain distance from the user's eyes and face. This is generally achieved through the use of a nose support that is mounted to the goggles and can be positioned on the user's nose such that a certain distance is maintained between the lens and the user's eyes and face. This gives rise to a conflict of objectives between maintaining clear space (to avoid the pane fogging up or obstructing the user's eyelashes) and protecting the eyes from unwelcome products from the surrounding environment.

BRIEF SUMMARY OF THE INVENTION

The invention was concerned with developing an enhanced pair of protective goggles that ensure enhanced protection of the eyes while also providing sufficient ventilation and without compromising the user's comfort.

The objective underlying the invention was achieved in the form of a pair of protective goggles with the characteristics named in claim 1. These have the advantage that edge of the lens is positioned particularly close to the user's face while still guaranteeing a degree of clear space that permits sufficient ventilation and a high degree of wearer comfort. With the embodiment of the lens according to the invention, the lens may, without requiring additional equipment, be realized affordably and in a manner that increases comfort for the user. According to the invention, it is intended that each lens section has a first and a second line of curvature that, at least in substantial part, are positioned transversely to one another and along which the lens section extends, and that the lines of curvature of each section are inclined towards the lines of curvature of the respective other section in their positioning. As such, each section of the lens extends along two lines of curvature positioned transversely to one another; in particular, this is intended to produce a curve in each section of the lens that, when the goggles are worn as intended, protrudes in front of the user's face.

This means that each eye is assigned its own curve, which in turn means that each section of the lens is optimally adapted to the shape of the user's face. Due the fact that the lines of curvature of each of the two lens sections are inclined towards each other, the curve of each section is slanted or tilted towards the curve of the respective other section. This facilitates the particularly favorable adaptation of the lens sections to the natural shape of the face, since it ensures, in particular, that the distance between the lens and the user's face is, at least in substantial part, the same along the entire edge of the lens. In particular, the first line of curvature and the second line of curvature are each curved in only one dimension; which means that when the lens is viewed from the top, the lines of curvature run in a linear fashion and thus that in a plan view drawing of the lens, they can be represented as straight lines that intersect one another. The curve achieved by the two lines of curvature also means that the middle region of each lens section is positioned at a great enough distance from the user's eye that the user's eyelashes do not collide with it. Thanks to the curve, the lens is located far away enough from the user's eyes that the user can move (i.e. open and close) their eyelids without their eyelashes colliding with the lens material. Only the edges of each lens section are located in close proximity to the user's face, which significantly increases comfort for the wearer. Since the lines of curvature of each section of the lens are inclined towards the lines of the respective other section in their positioning, the first line of curvature does not run on an exactly horizontal course, but is rather inclined towards the horizontal.

According to a preferred further form of the invention, the first line of curvature, which runs through the area between the upper and lower edges of the goggles on each side, is—in substantial part—horizontal. In this context, a "horizontal extension" is a line that, when the glasses are worn as intended, extends from one of the user's eyes towards the other; i.e. is horizontal when the user is facing straight ahead. As such, the first line of curvature ensures that the side edges of the lens sit close to the user's face and the lens follows the basic curve of the user's head along the horizontal plane.

In a particularly preferred form of the invention, the first lines of curvature are inclined towards one another in such a way that they converge towards the upper edge. This means that the curvatures of the individual lens sections are positioned favorably in relation to the user's nasal bridge and run diagonally towards one another the direction of the nasal bridge. As a result, the curvatures extend to a point that is particularly close to the central vertical axis of the lens above the nasal region, which ensures the advantageous adaptation of the lens to the shape of the user's face in the area of the nose support, too.

Furthermore, it is preferred that the second line of curvature, which runs from the upper edge of the goggles to the lower edge on each of the sections, is—at least in substantial part—vertical. As such, the second line of curvature, which is positioned transversely to the first line of curvature, runs from the upper edge to the lower edge and thus—when the glasses are worn as intended—in a vertical direction, affording the lens a certain curvature between the upper and lower edges. Thanks to this curvature, the lower edge ends in close proximity to the wearer's cheek, which means that the abovementioned advantageous reduction in space between the head and the edge of the goggles is achieved. It is possible for the second line of curvature of each section to extend in a precisely vertical fashion such that the two lines of curvature are positioned parallel to one another; however, it is preferred that the second lines of curvature should also be inclined towards one another and should each be positioned at the same angle to their corresponding first line of curvature.

It is preferred that the intersection point of the first and second lines of curvature of each lens section is located, at least in substantial part, in the middle of the respective lens section of the lens. This means that the curvature exhibited by each sections of lens is positioned advantageously in relation to the user's eye on each side, which leads, in particular, to vision-related benefits for the user when viewing things through the lens. In particular, the abovementioned advantage ensures that all parts of the lens are positioned at an equal distance from the user's eyes and, in particular, from their eyelashes.

It is further preferred that the two lens sections of the goggles are embodied by separate lenses, each of which is securely connected to the other, in particular by a nose support. This facilitates cost-effective production and the simple assembly of the protective goggles with optimal capacity for adaptation to the user's face.

Alternatively, the protective goggles may be embodied by one continuous lens pane that is used to form both sections. This results in a particularly stable pair of protective goggles with two sections of lens, each of which is curved in two directions and is inclined towards the respective another in its embodiment as described above.

Preferably, the second line of curvature of each section should intersect its respective first line of curvature in a vertical fashion. This means that each lens section has a center of curvature at which both lines of curvature meet and at which the two curvatures are aligned perpendicular to one another. This results in each section of the lens having, in substantial part, a semi-spherical contour.

According to a preferred form of the invention, the first line of curvature one each section should be positioned such that it is inclined towards the horizontal axis of the protective goggles at an angle of 5° to 30°, in particular at an angle of 10° to 14° and preferably at an angle of 12°. This means that the horizontal line of curvature does not run exactly horizontally, but rather is inclined towards the horizontal axis, which in turn ensures that the outer side edge of the lens occupies an advantageous position in the cheek area in relation to the user's face. In particular, the first lines of curvature mirror each other on the central vertical axis of the protective goggles in their embodiment, which means that the protective goggles as a whole are mirror-symmetrical.

Furthermore, according to a preferred form of the invention, the first line of curvature of each section has a radius of 43 to 63 mm, in particular of 50 mm to 56 mm and preferably of 53 mm. This achieves an advantageous curvature that, in turn, ensures the advantageous fit of the protective goggles to the face for the vast majority of the human population.

In a particularly preferred form of the invention, the second line of curvature on each section has a radius of 30 mm to 50 mm, in particular of 35 mm to 45 mm and preferably of 40 mm. This ensures the advantageously close positioning of, in particular, the lower edge of the protective goggles in relation to the user's face; this ensures a sufficient air gap while maintaining optimal protection and comfort for the wearer.

According to a preferred further form of the invention, the lens features a nose support on its lower edge as already described above. It is preferred that the goggles have a flexible elastic protective lip, located only on the lower edge of the lens, that extends from the nose outwards in the direction of at least one of the outer side edges of the lens and from the lower edge of the lens downwards, serving as an extension of the lens to the support on the user's cheek. The protective lip ensures that any opening or gaps between the protective goggles and the user's cheek are bridged and thus that the penetration of (e.g.) particles of dirt into the space between the goggles and the user's eyes is prevented. The fact that the protective lip extends only along the lower edge of the lens ensures that there is sufficient exchange of ambient air in the areas around the side edges and the upper edge, which, for example, prevents the goggles fogging up. Because the protective lip extends downwards to the pad on the user's cheek by way of extension of the lens, this gives rise to a protective lip that sits particularly flush to the cheek and extends in the direction of an area in which a respiratory mask can additionally be placed. As part of this system, the respiratory mask can be placed optionally over the protective lip such that the protective lip and respiratory mask overlap and protect the face and eyes while simultaneously ensuring the secure positioning of both the protective lip and the respiratory mask on the user's face. The advantageous embodiment of the protective goggles means that the lens is located particularly close to the user's face and the respiratory mask located particularly close to the user's eye area, which facilitates the advantageous fit of the respiratory mask on the user's face. This also reduces the risk of collision between the protective goggles and the respiratory mask (or other protective equipment), meaning that both can be worn comfortably and without requiring the user to sacrifice their comfort.

According to a preferred further form of the invention, the protective lip forms or contributes to forming the nose support of the protective goggles. To this end, either one protective lip is provided for each of the user's eyes—each of which, preferably, is integrally molded or otherwise attached to its own separate lens—or else the protective lip extends along the entire lower edge of the protective goggles, across both lens section, and thus forms the nose support in the in the middle. In this case, the protective lip is embodied integrally with the nose support. Preferably, the nose support is, at least in substantial part, embodied on the side of the protective goggles not facing the user's face, which in turn means that the lenses sit particularly close to the face. According to one particular embodiment, this is achieved by the protective lip extending from straight down the lower edge of the lens in one plane, whereby its curve follows that of the first horizontal line of curvature. Alternatively, the protective lip may have its own curvature along a horizontal axis, which would cause the lip to bend in such a way that it lies flush to the user's cheek.

The protection system according to the invention, with the features described in the claims, is characterized by the design of the protective goggles according to the invention. This gives rise, as a minimum, to the aforementioned advantages. In addition, the advantageous embodiment of the protective goggles means that the protective mask sits particularly close to the user's eyes and, more specifically, to the protective goggles, and thus ensures a high degree of comfort for the wearer. In particular, the protective goggles are adapted to the shape of the respiratory protection mask to guarantee the optimal fit of both on the user's face and without allowing these to impinge on or collide with on another during wear in such a way that the optimal fit of the affected section is hindered.

It is particularly preferred that that the protective goggles have the aforementioned protective lip, whereby this protective lip preferably features a support area for the mask. It is preferred that this support area is embodied as a sliding-contact zone, so that any movement of the respiratory mask on the user's face does not lead to the movement of the protective goggles.

BRIEF DESCRIPTION OF THE DRAWINGS

The invention is described in greater detail in the drawings, whereby each figure shows the following.

DETAILED DESCRIPTION OF THE INVENTION

Figure 1:
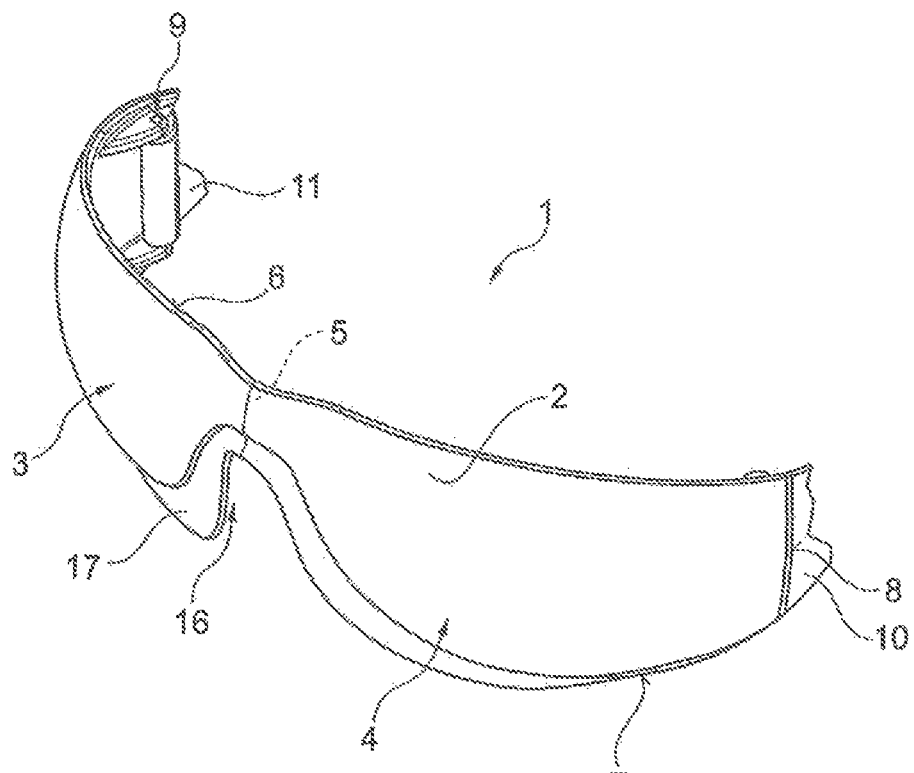
FIG. 1. A perspective view of the advantageous pair of protective goggles.

FIG. 1 shows a perspective view of an advantageous pair of protective goggles (1) for human use. The protective goggles (1) have a lens (2) made particularly from transparent material and forming two lens sections (3,4), whereby each of the lens sections (3,4) is assigned to one of the user's eyes. The lens (2) is embodied as a continuous lens that is used to form both lens sections (3,4). An alternative design in which each lens section (3,4) is formed by its own individual lens is foreseen according to a further embodiment of the invention and is indicated in FIG. 1 by a dashed central dividing line (5).

The lens (2) has an upper edge (6) that is positioned against the user's forehead, a lower edge (7) positioned against the user's cheeks and two outer side edges (8 and 9), each of which is connected to a temple (10, 11) to allow it to be supported on the user's ear. The temples (10, 11) are only partially shown here.

The lens (2) of the advantageous protective goggles (1) is embodied in such a way that each lens section (3, 4) extends along two lines of curvature, where the lines in each section are positioned transversely and, in particular, perpendicular to one another.

Figure 2:
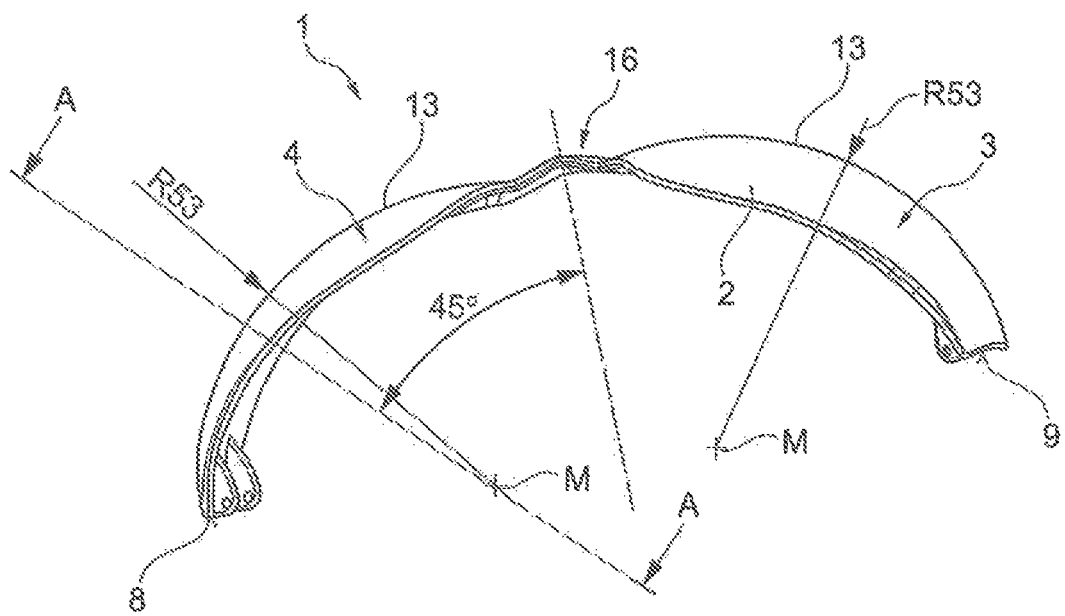
FIG. 2. A perspective plan view of the protective goggles from above.

FIG. 2 shows a plan view of the protective goggles (1). In the plan view, it can be seen that both sections of lens (3, 4) have a first curvature. This means that each of the lens sections (3, 4) extends along a first line of curvature (13) that runs, in substantial part, horizontally along the lens (2). The first lines of curvature (13) are embodied in such a way that they are convex relative to the center of curvature M, which, when the goggles are worn correctly, is located over the user's eye. In the present case, each first line of curvature (13) has a radius of 53 mm, whereby in FIG. 2, only the radius for lens section (4) is shown.

Figure 3:
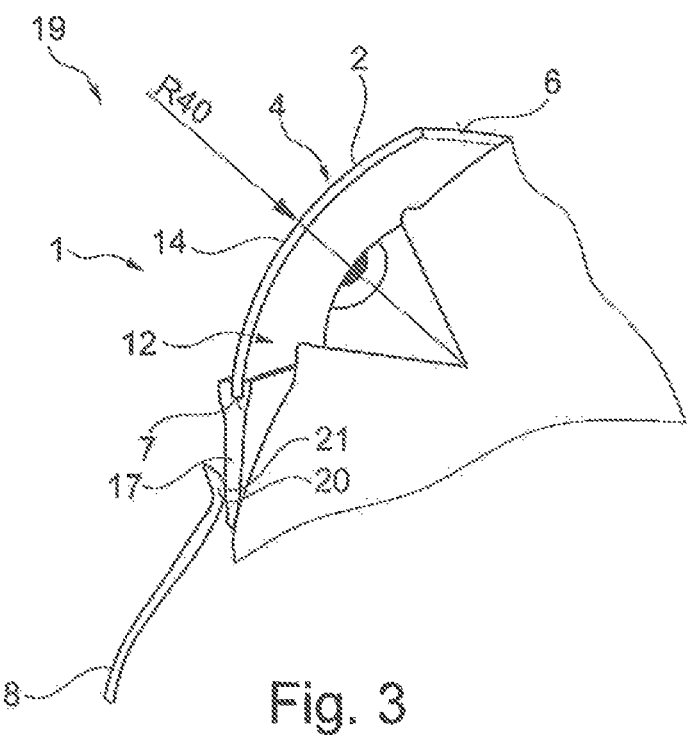
FIG. 3. A sectional drawing of the protective goggles.

FIG. 3 shows a sectional drawing of the protective goggles (1) from FIG. 2 along line A-A. The sectional drawing shows clearly that the lens (2), in particular lens section (4), has a second line of curvature (14) that extends transversely to the first line of curvature (13). FIG. 3 also illustrates the positioning of the protection goggles (1) on the eye (12) of a user, who is not shown in further detail here.

Figure 4:
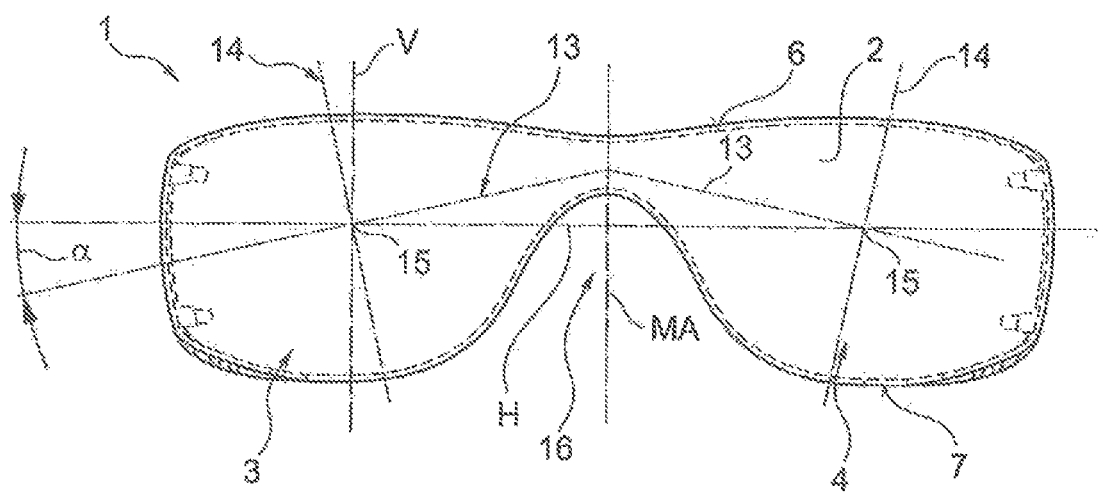
FIG. 4. A plan view of the protective goggles from the front.

FIG. 4 shows a plan view of the front side of the protective goggles (1). Dotted lines are used to mark the lines of curvature (13, 14) on lens section (4), which intersect each other roughly in the middle of lens section (4)—at point 5—and, in the present case, are positioned perpendicular to one another. The lines of curvature (13, 14) are each curved in only one dimension, which means that they are shown as straight lines on the plan view shown in the figure. FIG. 4 shows projections of the curvature lines (13, 14) on this basis. In addition, the first line of curvature (13) is inclined at an angle α of, in the present case, α=12° to the horizontal H, so that the position of the first line of curvature (13) on the plan view is rotated counterclockwise by the angle α. This means that the intersection point (15) lies roughly in the middle of lens section (4) and that the first line of curvature (13) runs above a recess on the lower edge (7) of the lens (2) that forms a nose support (16) in the transition to the adjacent lens section (3).

Because the line of curvature (14) is positioned perpendicular to the line of curvature (13), the second line of curvature (14) is also inclined, in particular in the direction of a vertical axis V.

The first and second lines of curvature (13, 14) assigned to lens section (3) are a mirror image of the lines of curvature (13, 14) of lens (4), which means that there is reflection about a vertical central axis MA that, in FIG. 4, runs vertically down the middle of the lens (2) as shown by the illustrative dividing line (5).

The lens sections (3, 4), which extend only along the lines of curvature (13, 14), are thus curved in two different directions in their embodiment, which results in each section having, at least in substantial part, a semi-spherical contour. In the present case, the respective first line of curvature (13) has a radius of 53 mm (R53). The respective second line of curvature (14), in contrast, has a preferred radius of 40 mm (R40).

Thanks to the advantageous course of the first line of curvature (13), the lens (2) encloses the user's face in an advantageous fashion at the sides. Thanks to the advantageous course of the second line of curvature (14), the individual lens sections (3, 4) extend advantageously from the forehead of the user (i.e. from the upper edge (6)) to the user's cheek (i.e. to the lower edge (7)) in such a way that the lens is positioned only a small distance from the user's face at both the upper (6) and lower (7) edges. On the one hand, this small distance ensures that sufficient air exchange can take place, preventing the lens (2) from fogging up; on the other hand, the distance is small enough to protect the user's eyes from, for example, chips or liquids that may be projected in the direction of the user during the machining of a work piece. In particular, the second curve along the second line of curvature (14) means that the individual lens sections (3, 4) curve in front of the respective eye (12) of the user in such a way that a small distance is guaranteed at the edges and that there is a sufficiently large distance from the eye in the central area to prevent the user from hitting the protective goggles (1) with—for example—their eyelashes, as indicated in FIG. 3. Thanks to the advantageous double-curved design of the lens sections (3, 4), space is afforded for the movement of eyelids and eyelashes without also resulting in a large amount of clear space between the edges of the lens (2) and the user's face.

Due to the inclination of the first lines of curvature [13] towards one another in such a way that they converge in the direction of the upper edge (6)—in particular, due to the obtuse angle between the two lines—the respective curve of each lens section (3, 4) extends in an advantageous fashion in the nasal region; specifically, in the direction of the nose support attached to the lens (2). In particular, this means that the first lines of curvature (13) end above the nose/nose support, which in turns ensures the advantageous adaptation of the respective lens section to the shape of the user's face.

To further reduce the already-small distance between the lower edge (7) and the user's cheek, the protective goggles (1) may optionally feature a protective lip (17). The protective lip (17) is located only on the lower edge (7) and, in the present case, extends integrally from lens section (4) to lens section (3), thereby helping to form the nose support (16). In addition, the protective lip (17) extends downwards as an extension of the lens (2)—that is, it extends downwards from the lower edge (7) as an extension of the lens such that, when the goggles are worn as intended, the protective lip (17) rests on the user's cheek and thus that the gaps between the lower edge (7) and the user's cheek are completely closed or sealed, thereby securely preventing the penetration of dirt particles, chips, fluid or similar into this area. Optionally, the protective lip (17) may be made from transparent material so as to avoid further limiting the user's sight. In particular, the protective lip (17) is integrally molded directly to the lens (2) and, in particular, is positively bonded thereto thereby guaranteeing the secure attachment of the protective lip (17) to the lens (2) in the long term.

Advantageously, the protective lip (17) is embodied such that it forms the nose support (16) in such a way that the nose support (16), at least in substantial part, is embodied on the side of the lens (2) facing away from the user's face; that is, protruding outwards from the lens (2). This has the effect that the lens (2) is positioned particularly close to the user's face.

While, according to the present form of the invention, the first lines of curvature (13) are inclined at an angle α of 12° to the horizontal H, it has generally been observed that an incline of 5° to 30° and in particular of 10° to 14° is, in principle, suitable for ensuring the advantageous embodiment of the protective goggles. The same applies for the radii named herein, which are given as 53 mm for the first line of curvature and 40 mm for the second line of curvature in the exemplary embodiment. As a general principle, however, the radii may deviate from these named radii up to a certain a degree. In particular, radii of 43 to 63 mm and more particularly of 50 to 60 mm have shown to be advantageous for the first line of curvature (13). For the second line of curvature (14), radii of 30 to 50 mm and more particularly of 35 to 45 mm have been shown to be advantageous.

Optionally, the protective goggles (1) may be combined with a respiratory protection mask (18) to produce a protection system (19) as shown in FIG. 3. The respiratory protection mask (18) is embodied in such a way that it extends over the mouth and nose of the user when worn as intended and fits tightly to the user's face at its outer edge (2). If the protective lip is provided (17), this serves at least as a partial support for the outer edge (20) of the respiratory mask (18). In particular, the protective lip (17) has a sliding-contact zone that faces away from the user's face and on which the respiratory mask (18) may be placed by aligning its outer edge (2) with the sliding-contact zone. The sliding-contact zone (21) allows the respiratory mask (18) to move around on the protective lip (17) without moving the protective goggles (1) on the user's face.

The advantageous design of respiratory mask (18) and protective goggles (1) means that overall a high level of wearer comfort is achieved for protection system (19) as a whole.

The invention claimed is:

1. A protective goggles comprising:
at least one lens comprising a respective lens section for each eye of a user when worn, each lens section having a first line of curvature and a second line of curvature, the first line of curvature and the second line of curvature oriented at least substantially transversely to one another, and along which the respective lens section extends, and the first and second lines of curvature of one lens section being inclined with respect to the first and second lines of curvature of the other lens section.

2. The protective goggles of claim 1, wherein the respective first line of curvature extends substantially horizontally between an upper edge and a lower edge of the at least one lens.

3. The protective goggles of claim 2, wherein the first lines of curvature are inclined relative to one another in such a way that they converge in a direction of the upper edge.

4. The protective goggles of claim 1, wherein the second lines of curvature extend substantially vertically from an upper edge to a lower edge of the at least one lens.

5. The protective goggles of claim 1, wherein an intersection point of the first and second lines of curvature of each lens section is located, at least in substantial part, in a middle of the respective lens section of the lens.

6. The protective goggles of claim 1, wherein a respective lens section of the lens that is assignable to one eye of the user when worn is embodied as a separate lens to the lens section that is assignable to the other eye of the user when worn.

7. The protective goggles of claim 1, wherein both lens sections are formed integrally into one continuous lens.

8. The protective goggles of claim 1, wherein each second line of curvature intersects the corresponding first line of curvature in an orthogonal fashion.

9. The protective goggles of claim 1, wherein each first line of curvature is inclined with respect to a horizontal axis (H) of the protective goggles at an angle in a range of 5° to 30°.

10. The protective goggles of claim 9, wherein each first line of curvature is inclined with respect to a horizontal axis (H) of the protective goggles at an angle in a range of 10° to 14°.

11. The protective goggles of claim 10, wherein each first line of curvature is inclined with respect to a horizontal axis (H) of the protective goggles at an angle of 12°.

12. The protective goggles of claim 1, wherein each first line of curvature has a radius in a range of 43 mm to 63 mm.

13. The protective goggles of claim 12, wherein each first line of curvature has a radius in a range of 50 mm to 56 mm.

14. The protective goggles of claim 13, wherein each first line of curvature has a radius of 53 mm.

15. The protective goggles of claim 1, wherein each second line of curvature has a radius in a range of 30 mm to 50 mm.

16. The protective goggles of claim 1, wherein each second line of curvature has a radius in a range of 35 mm to 45 mm.

17. The protective goggles of claim 16, wherein each second line of curvature has a radius of 40 mm.

18. The protective goggles of claim 1, further comprising a nose support located on a lower edge of the lens.

19. The protective goggles of claim 1, further comprising an elastically deformable protective lip located on a lower edge of the lens.

20. The protective goggles of claim 19, wherein the protective lip extends from the lower edge of the lens as an extension of the lens and is supportable by a user's cheek when worn.

21. The protective goggles of claim 19, wherein the protective lip forms or contributes to forming a nose support.

22. The protective goggles of claim 19, wherein the protective lip includes a sliding zone for supporting a respiratory mask in a region of the sliding zone.

23. A wearable protective system including a respiratory mask and a protective googles, wherein the protective goggles include at least one lens comprising a respective lens section for each eye of a user when worn, each lens section having a first line of curvature and a second line of curvature, the first line of curvature and the second line of curvature oriented at least substantially transversely to one another, and along which the respective lens section extends, and the first and second lines of curvature of one lens section being inclined with respect to the first and second lines of curvature of the other lens section.

* * * * *